United States Patent
Kuroda et al.

(10) Patent No.: US 11,123,410 B2
(45) Date of Patent: Sep. 21, 2021

(54) INTESTINAL FLORA IMPROVEMENT AGENT

(71) Applicants: AMANO ENZYME INC., Nagoya (JP); HIROSHIMA UNIVERSITY, Higashihiroshima (JP)

(72) Inventors: Manabu Kuroda, Kakamigahara (JP); Shotaro Yamaguchi, Kakamigahara (JP); Norihisa Kato, Higashihiroshima (JP)

(73) Assignees: AMANZO ENZYME INC., Nagoya (JP); HIROSHIMA UNIVERSITY, Higashihiroshima (JP)

( * ) Notice: Subject to any disclaimer, the term of this patent is extended or adjusted under 35 U.S.C. 154(b) by 127 days.

(21) Appl. No.: 15/999,363

(22) PCT Filed: Feb. 17, 2017

(86) PCT No.: PCT/JP2017/005985
§ 371 (c)(1),
(2) Date: Aug. 17, 2018

(87) PCT Pub. No.: WO2017/142079
PCT Pub. Date: Aug. 24, 2017

(65) Prior Publication Data
US 2019/0091301 A1 Mar. 28, 2019

(30) Foreign Application Priority Data

Feb. 18, 2016 (JP) .............................. JP2016-028941

(51) Int. Cl.
| | |
|---|---|
| *A61K 38/47* | (2006.01) |
| *A61K 36/062* | (2006.01) |
| *A23L 33/195* | (2016.01) |
| *A23L 29/00* | (2016.01) |
| *A23L 33/135* | (2016.01) |
| *A23L 2/52* | (2006.01) |
| *A61K 9/00* | (2006.01) |

(52) U.S. Cl.
CPC .............. *A61K 38/47* (2013.01); *A23L 29/06* (2016.08); *A23L 33/135* (2016.08); *A23L 33/195* (2016.08); *A61K 36/062* (2013.01); *C12Y 302/01001* (2013.01); *A23L 2/52* (2013.01); *A23V 2002/00* (2013.01); *A61K 9/0053* (2013.01)

(58) Field of Classification Search
CPC .... A61K 38/47; A61K 36/062; A61K 9/0053; A23L 33/195; A23L 29/06; A23L 33/135; A23L 2/52; C12Y 302/01001; A23V 2002/00; A61P 37/08; A61P 37/04; A61P 35/00; A61P 29/00; A61P 1/16; A61P 1/14; A61P 1/04
See application file for complete search history.

(56) References Cited

U.S. PATENT DOCUMENTS

| | | | |
|---|---|---|---|
| 6,042,823 A | 3/2000 | Kimura et al. | |
| 2009/0155417 A1 | 6/2009 | Kadota et al. | |
| 2013/0280375 A1 | 10/2013 | Kreisz et al. | |
| 2013/0330307 A1 | 12/2013 | Millan | |
| 2013/0330308 A1 | 12/2013 | Millan et al. | |
| 2014/0234279 A1 | 8/2014 | Millan | |

FOREIGN PATENT DOCUMENTS

| | | |
|---|---|---|
| JP | 2000-325045 A | 11/2000 |
| JP | 2007-325580 A | 12/2007 |
| JP | 2010-004760 A | 1/2010 |
| JP | 2012-188372 A | 10/2012 |
| JP | 2014-507946 A | 4/2014 |
| WO | WO 2012/022745 A1 | 2/2012 |
| WO | WO 2016/071989 A1 | 5/2016 |

OTHER PUBLICATIONS

H. Uhlig (Industrial Enzymes and Their Applications, Helmut Uhlig, John Wiley & Sons, Apr. 6, 1998—Technology & Engineering—472 pages, p. 429 Only, 3 pages of PDF.*
Effects of Aspergillus protease supplemented diets on intestinal luminal environment in rats, 68$^{th}$ The Japanese Society of Nutrition and Food Science Taikai Koen Yoshishu, p. 286, 3L-02a, 2014.
Gomi, K., et al., Cloning and Nucleotide Sequence of the Acid Protease-encoding Gene (pepA) from *Aspergillus oryzae*, Bioscience Biotechnology, and Biochemistry, vol. 57, No. 7, pp. 1095-1100, 1993.
International Search Report & Written Opinion, dated Apr. 25, 2017, in International Application No. PCT/JP2017/005985.
International Search Report & Written Opinion, dated Apr. 25, 2017, in International Application No. PCT/JP2017/005986.
Okazaki, Y., et al., Burdock Fermented by *Aspergillus awamori* Elevates Cecal *Bifidobacterium*, and Reduces Fecal Deoxycholic Acid and Adipose Tissue Weight in Rats Fed a High-Fat Diet, Bioscience, Biotechnology, and Biochemistry, vol. 77, No. 1, pp. 53-57, 2013.
Yang, Y., et al., Beneficial effects of protease preparations derived from *Aspergillus* on the colonic luminal environment in rats consuming a high-fat diet, Biomedical Repots, vol. 3, pp. 715-720, 2015.
Yi, J.Q., et al., The Effects of Enzyme Complex on Performance, Intestinal Health and Nutrient Digestibility of Weaned Pigs, Asian-Australasian Journal of Animal Sciences, vol. 26, No. 8, pp. 1181-1188, 2013.
Zhang, G.G., et al., Effects of dietary supplementation of multi-enzyme on growth performance, nutrient digestibility, small intestinal digestive enzyme activities, and large intestinal selected microbiota in weanling pigs, Journal of Animal Science, vol. 92, pp. 2063-2069, 2014.

* cited by examiner

*Primary Examiner* — Kade Ariani
(74) *Attorney, Agent, or Firm* — Knobbe, Martens, Olson & Bear LLP

(57) ABSTRACT

The purpose of the present invention is to provide an agent for improving intestinal flora which can increase the number of beneficial bacteria such as lactic acid bacteria and *Bifidobacterium* to improve intestinal flora by using an enzyme. An amylase that is derived from a microorganism belonging to *Aspergillus* can increase beneficial bacteria such as lactic acid bacteria and *Bifidobacterium* in intestines to exert an excellent effect of improving intestinal flora.

2 Claims, No Drawings

Specification includes a Sequence Listing.

SEQUENCE LISTING

<160> NUMBER OF SEQ ID NOS: 4

<210> SEQ ID NO 1
<211> LENGTH: 17
<212> TYPE: DNA
<213> ORGANISM: Artificial Sequence
<220> FEATURE:
<223> OTHER INFORMATION: Synthetic - Forward primer for detecting Bifidobacterium spp.

<400> SEQUENCE: 1
cgcgtcyggt gtgaaag          17

<210> SEQ ID NO 2
<211> LENGTH: 18
<212> TYPE: DNA
<213> ORGANISM: Artificial Sequence
<220> FEATURE:
<223> OTHER INFORMATION: Synthetic - Reverse primer for detecting Bifidobacterium spp.

<400> SEQUENCE: 2
ccccacatcc agcatcca          18

<210> SEQ ID NO 3
<211> LENGTH: 22
<212> TYPE: DNA
<213> ORGANISM: Artificial Sequence
<220> FEATURE:
<223> OTHER INFORMATION: Synthetic - Forward primer for detecting Lactobacillus spp.

<400> SEQUENCE: 3
gaggcagcag tagggaatct tc          22

<210> SEQ ID NO 4
<211> LENGTH: 27
<212> TYPE: DNA
<213> ORGANISM: Artificial Sequence
<220> FEATURE:
<223> OTHER INFORMATION: Synthetic - Reverse primer for detecting Lactobacillus spp.

<400> SEQUENCE: 4
ggccagttac tacctctatc cttcttc          27

INTESTINAL FLORA IMPROVEMENT AGENT

PRIORITY AND CROSS REFERENCE TO RELATED APPLICATIONS

This application is a U.S. National Phase Application under 35 U.S.C. § 371 of International Application No. PCT/JP2017/005985, filed Feb. 17, 2017, designating the U.S. and published as WO 2017/142079 A1 on Aug. 24, 2017, which claims the benefit of Japanese Patent Application No. 2016-028941, filed Feb. 18, 2016. All applications for which a foreign or a domestic priority is claimed are identified in the Application Data Sheet filed herewith and are hereby incorporated by reference in their entirety under 37 C.F.R. § 1.57.

REFERENCE TO THE ELECTRONIC SEQUENCE LISTING

The present application is being filed along with an Electronic Sequence Listing as an ASCII text file via EFS-Web. The Electronic Sequence Listing is provided as a file entitled LEX024001APCSEQLIST.txt, created and last saved on Aug. 16, 2018, which is 1,236 bytes in size.

TECHNICAL FIELD

The present invention relates to an agent for improving intestinal flora which can increase the number of beneficial bacteria such as lactic acid bacteria and *Bifidobacterium* to improve intestinal flora.

BACKGROUND

Recently, causal relationships between intestinal environment and various diseases are intensively investigated to reveal that improvement of intestinal environment is effective in preventing or ameliorating various diseases. In intestine, beneficial bacteria such as lactic acid bacteria and *Bifidobacterium* and bad bacteria such as *Escherichia coli* are present in a mixed manner. Forming beneficial bacteria-dominated flora is important in order to form a healthy intestinal environment.

Conventionally, probiotics, prebiotics, and the like are developed, and various materials by which beneficial bacteria become predominant to improve intestinal flora are proposed. It is also reported that administration of digestive enzymes such as amylases and proteases can also improve intestinal flora. For example, Non-Patent Document 1 discloses that in a pig which is fed with a specific enzyme blend consisting of an amylase, a protease, and a xylanase together with animal feed, the number of *Lactobacillus* is increased and the number of *Escherichia coli* is decreased in the large intestine. Non-Patent Document 2 also discloses that in a pig which is fed with a specific enzyme blend (Nopcozyme II; Diasham Resources Pte Ltd.) consisting of an amylase derived from *Bacillus amyloliquefaciens*, a protease derived from *Bacillus subtilis*, and a xylanase derived from *Trichoderma* together with animal feed, the number of *Lactobacillus* is increased and the numbers of *Salmonella* and *Escherichia coli* are decreased. Non-Patent Document 3 further discloses that a neutral protease derived from *Aspergillus* and an acid protease derived from *Aspergillus niger* increase the number of bacteria of *Lactobacillus* spp. and/or bacteria of *Bifidobacterium* spp. in intestines of rats.

Thus, as an enzyme preparation which can improve intestinal flora, specific enzyme blends consisting of an amylase, a protease, and a xylanase are conventionally known. However, it has not been shown that which enzyme of these enzymes contributes to the improvement of intestinal flora. Further, there is a drawback that use of such enzyme blends leads to increases in cost of producing the enzymes. On the other hand, although any one of a neutral protease derived from *Aspergillus* and an acid protease derived from *Aspergillus niger* alone can improve intestinal flora, no other enzyme which can improve intestinal flora when used alone has been revealed.

REFERENCES

Non-Patent Document 1: Yi et al., Asian Astralas. J. Anim. Sci., 2013, 26: 1181-1188

Non-Patent Document 2: Zhang et al., J. Amin. Sci., 2014, 92: 2063-2069

Non-Patent Document 3: Yang et al., Biomedical Reports, 2015, 3: 715-720

SUMMARY

Recently, in connection with increasing interest in health promotion, development of new materials by which beneficial bacteria become predominant to improve intestinal flora is desired. However, with respect to an agent for improving intestinal flora using an enzyme, no effective enzyme except for the conventionally reported enzyme preparations can be estimated even by analogy under the current circumstances.

Under the circumstances, an object of the present invention is to provide an agent for improving intestinal flora which can increase the number of beneficial bacteria such as lactic acid bacteria and *Bifidobacterium* to improve intestinal flora by using an enzyme.

The present inventors have made extensive investigations to solve the above problem and found that an amylase derived from a microorganism belonging to *Aspergillus* can increase beneficial bacteria such as lactic acid bacteria and *Bifidobacterium* in intestines to exert an excellent effect of improving intestinal flora. The present inventors have made further investigations based on the findings, leading to the completion of the invention.

Thus, the present invention includes the following aspects.

Item 1. An agent for improving intestinal flora comprising an amylase derived from a microorganism belonging to *Aspergillus* as an active ingredient.

Item 2. The agent for improving intestinal flora according to Item 1, wherein said amylase is derived from *Aspergillus oryzae*.

Item 3. The agent for improving intestinal flora according to Item 1 or 2, wherein said amylase is an alpha-amylase.

Item 4. A drug for oral administration for improving intestinal flora, comprising an agent for improving intestinal flora according to any one of Items 1 to 3.

Item 5. A food additive for improving intestinal flora, comprising an agent for improving intestinal flora according to any one of Items 1 to 3.

Item 6. Food or drink for improving intestinal flora, comprising an agent for improving intestinal flora according to any one of Items 1 to 3.

Item 7. A method for improving intestinal flora, comprising orally applying an amylase derived from a microorganism belonging to *Aspergillus* to a person who requires improvement of intestinal flora.

Item 8. The method for improving intestinal flora according to Item 7, wherein said amylase is derived from *Aspergillus oryzae*.
Item 9. The method for improving intestinal flora according to Item 7 or 8, wherein said amylase is an alpha-amylase.
Item 10. An amylase derived from a microorganism belonging to *Aspergillus* for use in a treatment for improving intestinal flora.
Item 11. The amylase according to Item 10, wherein said amylase is derived from *Aspergillus oryzae*.
Item 12. The amylase according to Item 10 or 11, wherein said amylase is an alpha-amylase.
Item 13. Use of an amylase derived from a microorganism belonging to *Aspergillus* for the manufacture of an agent for improving intestinal flora.
Item 14. The use according to Item 13, wherein said amylase is derived from *Aspergillus oryzae*.
Item 15. The use according to Item 13 or 14, wherein said amylase is an alpha-amylase.

The present invention can increase the number of beneficial bacteria such as lactic acid bacteria and *Bifidobacterium* and improve intestinal flora by using an amylase derived from a microorganism belonging to *Aspergillus*, and thus is effective in forming healthy intestinal environment, maintaining healthy intestinal environment, and preventing or treating a disease and/or symptom due in part to unhealthy intestinal environment.

DETAILED DESCRIPTION

1. Agent for Improving Intestinal Flora

An agent for improving intestinal flora of the present invention is characterized by containing an amylase derived from a microorganism belonging to *Aspergillus* as an active ingredient. The agent for improving intestinal flora of the present invention is described in detail below.

[Amylase]

In the agent for improving intestinal flora of the present invention, an amylase derived from a microorganism belonging to *Aspergillus* is used as an active ingredient. By selecting and using an amylase derived from a microorganism belonging to *Aspergillus*, beneficial bacteria such as lactic acid bacteria and *Bifidobacterium* in intestines can be increased and intestinal flora can be effectively improved.

In the agent for improving intestinal flora of the invention, the microorganism from which the amylase used is derived is not specifically limited as long as the microorganism belongs to *Aspergillus*. Examples include *Aspergillus oryzae, Aspergillus niger, Aspergillus sojae, Aspergillus saitoi*, and *Aspergillus luchuensis*. Inter alia, an amylase derived from *Aspergillus oryzae* has a prominent effect of increasing the number of beneficial bacteria such as lactic acid bacteria and *Bifidobacterium* in intestines, and thus is preferably used in the present invention.

In the agent for improving intestinal flora of the present invention, types of the amylases used are not specifically limited. Examples include an alpha-amylase, a beta-amylase, a glucoamylase, and an isoamylase. Inter alia, from the viewpoint of exerting far superior effect of improving intestinal flora, the alpha-amylase is preferred.

In the agent for improving intestinal flora of the present invention, the amylase derived from a microorganism belonging to *Aspergillus* can be used alone, or two or more amylases derived from different microorganisms and/or of different types can be used in combination.

The amylase used in the present invention may be either purified product or partially purified product containing other enzymes or the like together. In the agent for improving intestinal flora of the present invention, when the amylase derived from *Aspergillus oryzae* is used as a partially purified product, examples include an agent for improving intestinal flora containing no neutral protease according to a preferred aspect.

Among these amylases, from the viewpoint of exerting far superior effect of improving intestinal flora, preferred amylases include an alpha-amylase derived from *Aspergillus oryzae*. Examples of characteristics of an alpha-amylase derived from *Aspergillus oryzae* used in the present invention include characteristics satisfying the following (1) to (4).

(1) Action

It randomly hydrolyzes an alpha-1,4 bond of polysaccharides such as starch and glycogen. A mode of action is endo-type.

(2) Optimum pH

It has an optimum pH of around 5.0.

(3) Optimum Temperature

It has an optimum temperature of about 50° C.

(4) Molecular Weight

It has a molecular weight of 45,000±5,000 daltons as measured by SDS-PAGE.

The amylase used in the present invention can be prepared from a koji extract obtained by culturing a microorganism belonging to *Aspergillus* by a solid-state fermentation. Specifically, a microorganism belonging to *Aspergillus* is cultured by a solid-state fermentation, and then the culture extract is centrifuged, ultrafiltered, or the like to obtain supernatant liquid, as required, followed by concentration, purification, drying, or the like of the resulting supernatant liquid to obtain the amylase. In the preparation of the amylase, contamination of the obtained amylase with other enzymes can be prevented by, for example, a method including culturing using a medium which leads to specific production of only amylases, a method using alcohol precipitation which can precipitate only amylases, a method including separating amylases and other enzymes by ultrafiltration, and the like.

The amylase derived from a microorganism belonging to *Aspergillus* is also commercially available. In the agent for improving intestinal flora of the present invention, a commercially available amylase can be used as the amylase derived from a microorganism belonging to *Aspergillus*. Specifically, examples of the commercially available amylase include "Biozyme A" (a formulation of an amylase derived from *Aspergillus oryzae*, manufactured by Amano Enzyme Inc.), "Biodiastase" (a formulation of an amylase derived from *Aspergillus oryzae*, manufactured by Amano Enzyme Inc.), "Sumizyme L" (a formulation of an amylase derived from *Aspergillus oryzae*, manufactured by SHIN-NIHON CHEMICALS Corporation), and "GRINDAMYL A" (a formulation of an amylase derived from *Aspergillus oryzae*, manufactured by Danisco Japan Ltd.).

[Dose of Amylase]

The agent for improving intestinal flora of the present invention may be applied at a suitable dose as determined according to, for example, types of products in which the agent is used, applications, expected effects, and dosage forms. Examples of a daily dose for an adult human as an amount of the above amylase ingested or administered include 1 to 300,000 U, preferably 10 to 150,000 U, more preferably 10 to 100,000 U, even more preferably 50 to 50,000 U, still more preferably 50 to 15,000 U, most preferably 500 to 15,000 U. Herein, the amylase activity (U) is calculated by the following method.

(Method for Measuring Amylase Activity)

In a test tube, 10 mL of 1 wt % potato starch solution (pH 5.0) is placed and maintained at 37° C. Then, 1 mL of an enzyme solution (in water as a solvent) containing a sample which is to be measured for an amylase activity is added and allowed to stand at 37° C. for exactly 10 minutes, and then 2 mL of an alkaline tartrate solution (solution containing 10 wt % of sodium hydroxide and 34.6 wt % of potassium sodium tartrate tetrahydrate) and 2 mL of copper liquid (solution containing 6.932 wt % of copper sulfate pentahydrate) are added in this order. Then, the solution is immersed in boiling water for 15 minutes followed by cooling in flowing water, 2 mL of 37.5 wt % potassium iodide solution and 6-fold diluted concentrated sulfuric acid are added, and then the resulting solution is titrated with 0.05 mol/L sodium thiosulfate. As a blank, the enzyme solution is replaced with water (blank liquid). Under the above conditions, an amount of amylase which causes a reduction corresponding to 1 mg of glucose per minute is defined as 1 U. The following equations are used for the calculation.

Amount of amylase per 1 g or 1 mL of sample (U/g or U/mL)=Amount of glucose (mg)×1/10×1/$W$   [Equation 1]

Amount of glucose (mg)=($b-a$)×1.6×$f$ a: Titer (mL) as measured by using enzyme solution
b: Titer (mL) as measured by using blank liquid
1.6: 1 mL of 0.05 mol/L sodium thiosulfate solution corresponds to 1.6 mg of glucose.
1/10: Unit conversion factor of reaction time (min)
W: Amount of sample (g or mL) in 1 mL of enzyme solution
f: Factor of 0.05 mol/L sodium thiosulfate solution (for quantification)

[Use of Agent for Improving Intestinal Flora]

The agent for improving intestinal flora of the present invention can increase the number of beneficial bacteria such as *Bifidobacterium* and lactic acid bacteria in intestines by the effect of the above amylase to form a beneficial bacteria-dominated flora, and thus is used for the purpose of forming healthy intestinal environment, maintaining healthy intestinal environment, and the like. Specifically, the agent for improving intestinal flora of the present invention is superior in an effect of increasing the number of bacteria of *Bifidobacterium* spp. and *Lactobacillus* spp. in intestines, and thus can also be used as an agent for increasing the number of enteric bacteria of *Bifidobacterium* spp, and *Lactobacillus* spp. in intestines.

In addition, the agent for improving intestinal flora of the present invention can form a beneficial bacteria-dominated flora to form a healthy intestinal environment, and thus can also be used for the purpose of preventing or treating a disease and/or symptom due in part to unhealthy intestinal environment. Examples of the disease and/or symptom include decreased immunity, colorectal cancer, allergic disease, nonalcoholic steatohepatitis, obesity, and inflammatory bowel disease.

[Form for Using Agent for Improving Intestinal Flora]

The agent for improving intestinal flora of the present invention is orally applied by oral ingestion or oral administration. The agent for improving intestinal flora of the present invention is orally ingested or orally administered to exert an effect of improving intestinal flora after arriving at intestines, and thus can be blended for use with various products such as food and drink, drugs for oral administration, animal feed, and pet food.

When the agent for improving intestinal flora of the present invention is blended with the above various products, the products may contain probiotics and/or prebiotics as required together with the agent for improving intestinal flora of the present invention.

Examples of a microorganism used as the probiotics include lactic acid bacteria, *Bifidobacterium*, and *Bacillus subtilis* var *natto*. Specific examples of the lactic acid bacteria include lactic acid bacteria of *Lactobacillus* spp. such as *Lactobacillus casei*, *Lactobacillus acidophilus*, and *Lactobacillus plantarum*; lactic acid bacteria of *Enterococcus* spp. such as *Enterococcus faecalis*, *Enterococcus faecium*, and *Enterococcus hirae*; and lactic acid bacteria of *Streptococcus* spp. such as *Streptococcus bovis* and *Streptococcus thermophilus*. Specific examples of *Bifidobacterium* include *Bifidobacterium adolescentis*, *Bifidobacterium longum*, *Bifidobacterium bifidum*, *Bifidobacterium pseudolongum*, and *Bifidobacterium thermophilum*. These probiotics may be used alone or in combination of two or more.

Examples of the prebiotics include xylooligosaccharide, fructooligosaccharide, soybean oligosaccharides, isomaltooligosaccharide, lacto-fructo-oligosaccharides, galactooligosaccharides, and lactulose. These prebiotics may be used alone or in combination of two or more.

A formulation of a product with which the agent for improving intestinal flora of the present invention is blended may be any one of solid form, semi-solid form, liquid form, and the like, and is suitably selected according to types and applications of the product.

When the agent for improving intestinal flora of the present invention is used for food and drink, the above amylase is provided, as food and drink which exert an effect of improving intestinal flora, solely or in combination with other food materials or additives to be prepared in a desired form. Examples of the food and drink include a food for specified health uses, a nutritional supplement, a functional food, and a food for patients in addition to common food and drink. Forms of these foods and drinks are not specifically limited. Specific examples include supplements such as tablets, granules, powders, capsules, and soft capsules; and drinks such as energy drinks, fruit drinks, carbonated beverages, and lactic acid drinks.

When the agent for improving intestinal flora of the present invention is used for food and drink, an amount of the agent blended into the food and drink varies according to, for example, forms of the food and drink. In supplements, an amount of the above amylase is in a range of, for example, 0.3 to 100,000 U/g, preferably 3 to 50,000 U/g, more preferably 3 to 30,000 U/g, even more preferably 15 to 15,000 U/g, still more preferably 15 to 5,000 U/g, most preferably 150 to 5,000 U/g. In drinks, an amount of the above amylase is in a range of, for example, 0.003 to 1,000 U/mL, preferably 0.03 to 500 U/mL, more preferably 0.03 to 300 U/mL, even more preferably 0.15 to 150 U/mL, still more preferably 0.15 to 50 U/mL, most preferably 1.5 to 50 U/mL.

When the agent for improving intestinal flora of the present invention is used in the food and drink field, the agent for improving intestinal flora of the present invention can be provided, as a food additive, solely or in combination with other ingredients.

When the agent for improving intestinal flora of the present invention is used for drugs for oral administration, the agent for improving intestinal flora of the present invention is provided, as drugs for oral administration which exert an effect of improving intestinal flora, solely or in combination with, for example, other pharmacologically active ingredients, pharmaceutically acceptable bases, or additives to be prepared in a desired form. Forms of the drugs are not specifically limited. Specific examples include formulations for oral administration such as tablets, granules, powders, capsules, soft capsules, syrups, and liquids.

Examples of the bases and the additives used for manufacturing the drugs for oral administration include aqueous bases such as water and alcohol, oil-based bases, diluents, binders, filling agents, disintegrants, lubricants, algefacients, pH-adjusting agents, thickeners, antioxidants, sequestering agents, surfactants, emulsifiers, solubilizers, solubilizing agents, flavoring agents, and antiseptics.

When the agent for improving intestinal flora of the present invention is used as drugs for oral administration, ratio of the agent blended into the drugs for oral administration can be suitably determined according to, for example, forms of the drugs for oral administration within a range satisfying the above described dose. In drugs for oral administration in solid form or semi-solid form, an amount of the above amylase is in a range of, for example, 0.3 to 100,000 U/g, preferably 3 to 50,000 U/g, more preferably 3 to 30,000 U/g, even more preferably 15 to 15,000 U/g, still more preferably 15 to 5,000 U/g, most preferably 150 to 5,000 U/g. In drugs for oral administration in liquid form, an amount of the above amylase is in a range of, for example, 0.003 to 1,000 U/mL, preferably 0.03 to 500 U/mL, more preferably 0.03 to 300 U/mL, even more preferably 0.15 to 150 U/mL, still more preferably 0.15 to 50 U/mL, most preferably 1.5 to 50 U/mL.

When the agent for improving intestinal flora of the present invention is used for animal feed or pet food, the agent for improving intestinal flora of the present invention is provided, as animal feed or pet food which exerts an effect of improving intestinal flora, solely or in a desired form controlled in combination with other animal feed ingredients. Examples of the animal feed ingredients used for animal feed or pet food include cereal crops such as corn, wheat, barley, and rye; brans such as wheat bran and rice bran; dregs such as corn gluten meal and corn germ meal; animal-derived feed such as skimmed milk powder, whey, fish flour, and powdered bone; yeasts such as brewer's yeast; calciums such as calcium phosphate and calcium carbonate; vitamins; amino acids; and saccharides.

When the agent for improving intestinal flora of the present invention is used as animal feed or pet food, ratio of the agent blended into the animal feed or pet food varies according to, for example, forms and types of the animal feed or pet food, and types of animals for application. An amount of the above amylase is in a range of, for example, 0.003 to 1,000 U/g, preferably 0.03 to 500 U/g, more preferably 0.03 to 300 U/g, even more preferably 0.15 to 150 U/g, still more preferably 0.15 to 50 U/g, most preferably 1.5 to 50 U/g.

2. Other Aspects

As described above, an amylase derived from a microorganism belonging to *Aspergillus* has an effect of improving intestinal flora. Thus, the present invention further provides a method for improving intestinal flora comprising orally applying an amylase derived from a microorganism belonging to *Aspergillus* to a person who requires improvement of intestinal flora; an amylase derived from a microorganism belonging to *Aspergillus* for use in a treatment for improving intestinal flora; and use of an amylase derived from a microorganism belonging to *Aspergillus* for the manufacture of an agent for improving intestinal flora. The above specific aspects of the present invention are as described in the above section of "1. Agent for improving intestinal flora".

EXAMPLE

The present invention is described more specifically below with reference to Example, but it should not be construed to be limited to the example.

Test Example 1: Influence of Amylase Derived from *Aspergillus oryzae* on Intestinal Flora Using SD rats (male, 3 weeks old, from Hiroshima Institute for Experimental Animals), an influence of ingestion of Biozyme A (Amano Enzyme), which is an amylase formulation derived from *Aspergillus oryzae*, on intestinal flora was investigated. In the experiment, the rats were divided into 2 groups consisting of a control group and a working group (5 rats/group). The rats of each group were fed ad libitum for 14 days with animal feeds shown in Table 1.

The Biozyme A used in the experiment is a power formulation containing about 20 wt % of an alpha-amylase derived from *Aspergillus oryzae* having the following characteristics. The content of an alpha-amylase per total proteins contained in Biozyme A is 70 wt % or more, and it has been confirmed that no neutral protease is observed by SDS-polyacrylamide electrophoresis.

(Characteristics of Alpha-Amylase Contained in Biozyme A)

(1) Action

It randomly hydrolyzes an alpha-1,4 bond of polysaccharides such as starch and glycogen. A mode of action is endo-type.

(2) Optimum pH

It has an optimum pH of around 5.0.

(3) Optimum Temperature

It has an optimum temperature of about 50° C.

(4) Molecular Weight

It has a molecular weight of 45,000±5,000 daltons as measured by SDS-PAGE.

TABLE 1

| Ingredient | Control group % w/w | Working group % w/w |
| --- | --- | --- |
| Beef tallow | 30.00 | 30.00 |
| Casein | 20.00 (Net protein: 17.40) | 20.00 (Net protein: 17.40) |
| L-Cysteine | 0.30 | 0.30 |
| Cellulose | 5.00 | 5.00 |
| Vitamin Mix * | 1.00 | 1.00 |
| Mineral Mix * | 3.50 | 3.50 |
| Sucrose | 20.00 | 20.00 |
| Corn starch | 20.20 | 19.59 |
| Biozyme A | — | 0.61 |

* refers to a standard purified diet for mice and rats according to AIN-93 (American Institute of Nutrition (AIN)).

An amount of cecal contents of SD rats in each group was measured after 14-day feeding with the animal feed. Bacteria in the cecal contents of the SD rats were analyzed by real-time PCR using primers shown in Table 2 to calculate the number of *Bifidobacterium* (*Bifidobacterium* spp.) and lactic acid bacteria (*Lactobacillus* spp.) in intestines.

TABLE 2

| | Base sequences of primers used |
|---|---|
| For detecting Bifidobacterium spp. | Forward: CGCGTCYGGTGTGAAAG (SEQ ID NO: 1)<br>Reverse: CCCCACATCCAGCATCCA (SEQ ID NO: 2) |
| For detecting Lactobacillus spp. | Forward: GAGGCAGCAGTAGGGAATCTTC (SEQ ID NO: 3)<br>Reverse: GGCCAGTTACTACCTCTATCCTTCTTC (SEQ ID NO: 4) |

The results are shown in Table 3. There was no difference between the groups in amounts of the diet consumed, which showed that energy intakes were comparable between the groups. Thus, it should be noted that an accurate comparison between the groups is possible. In the working group, the numbers of *Bifidobacterium* and lactic acid bacteria in intestines were both higher than those in the control group.

That is, it was confirmed that ingestion of the amylase derived from *Aspergillus* promoted proliferation of *Bifidobacterium* and lactic acid bacteria, leading to improvement of intestinal flora. In addition, the amount of cecal contents in the working group was higher than that in the control group. The results supported that ingestion of the amylase derived from *Aspergillus* improved intestinal environment.

TABLE 3

| | | Control group | Working group |
|---|---|---|---|
| Amount of feeding (g/14 days) | | 175 ± 0 | 175 ± 0 |
| Weight of cecal contents (g) | | 1.25 ± 0.16 | 3.45 ± 0.32 |
| Intestinal flora | *Bifidobacterium* (% of total bacteria) | 0.25 ± 0.10 | 4.32 + 2.17 |
| | Lactic acid bacteria (% of total bacteria) | 5.5 ± 1.4 | 42.5 ± 7.0 |

What is claimed is:

1. A method of treatment for improving intestinal flora comprising administering an enzyme comprising an amylase derived from a microorganism belonging to *Aspergillus* to a person who requires improvement of intestinal flora, wherein the amylase exerts an effect of improving intestinal flora after arriving at intestines, wherein the enzyme consists of an *Aspergillus*-derived amylase.

2. The method according to claim 1, wherein said amylase is an alpha-amylase.

* * * * *